US006090391A

United States Patent [19]
Parkin

[11] Patent Number: 6,090,391
[45] Date of Patent: *Jul. 18, 2000

[54] RECOMBINANT TRYPTOPHAN MUTANTS OF INFLUENZA

[75] Inventor: Neil T. Parkin, Belmont, Calif.

[73] Assignee: Aviron, Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/604,757

[22] Filed: Feb. 23, 1996

[51] Int. Cl.[7] ........................ B61K 39/145; B61K 39/42; C07H 21/04

[52] U.S. Cl. ..................................... 424/206.1; 536/23.72; 424/159.1

[58] Field of Search .............................. 424/159.1, 206.1; 536/23.72

[56] References Cited

PUBLICATIONS

Nakagawa, The RNA Polymerase PB2 Subunit Is Not Required for Replication of the Influenza Virus Genome but Is Involved in Capped mRNA Synthesis, Feb. 1995, J. Virol 69(2):728–33.

Schonberger, Guillain–Barre syndrone: its epidemiology and associations with influenza vaccination, 1981, Annals of Neurology 9 Suppl:31–8.

Murphy, Use of Live Attenuated Cold–Adapter Influenza A Reassortant Virus Vaccines in Infants, children, Young Adults, and Elderly Adults, 1993, Inf Dis in Clin Prac 2:174–81.

Murphy & Chanock, Genetic Approaches to the Prevention of Influenza A Virus Infection, 1981, Genetic Variation Among Influenza Viruses, Academic Press, pp. 610–614.

Murphy, Genetic approaches to attenuation of influenza A virus for man, 1980, Phil Trans R Soc Lond B 288:401–15.

Murphy, Escape of a Highly Defective Influenza A Virus Mutant From Its Temperature Sensitive Phenotype by Extragenic Suppression and Other Types of Mutation, 1980, Annals NY Acad Sci, pp. 172–182.

Tolpin, Evaluation of a Phenotypic Repentant of the A/Alaska/77–ts–1A2 Reasortant Virus in Hamsters and in Seronegative Adult Volunteers etc, 1982, Infection and Immunity 36(2):645–50.

Lawson, Nucleotide Sequence Changes in the Polymerase Basic Protein 2 Gene of Temperature–Sensitive Mutants of Influenza A Virus, 1992, Virology 191:506–10.

Enami, Introduction of site–specific mutations into the genome of influenza virus, 1990, Proc Natl Acad Sci 87:3802–05.

Enami and Palease, High–Efficiency Formation of Influenza Virus Transfectants, 1991, J. Virol 65(5):2711–13.

Luytjes, Amplication, Expression and packaging of a Foreign Gene by Influenza Virus, 1989, Cell 59:1107–13.

Horimoto, Reverse Genetics Provides Direct Evidence for a Correlation of Hemagglutinin Cleavability and Virulence of an Avian Influenza A Virus, 1994, J Virol 68(5):3120–28.

Li, Influenza A Virus Transfectants with Chimeric Hemagglutinins containing Epitopes from Different Subtypes, 1992, J Virol 66(1):399–404.

Barclay, Influenza B Viruses with Site–Specific Mutations Introduced into the HA Gene, Feb 1995, J Virol 69(2):1275–79.

Yasuda, Growth Control of Influenza A Virus by M1 Protein etc, 1994, J Virol 68(12):8141–46.

Ishida, The Stacking Interactions in 7–Methylguanine–Tryptophan systems etc, 1993, Biochem and Biophys Res Comm 115(3):849–54.

Altmann, Site–directed Mutagenesis of the Tryptophan Residues in Yeast Eukaryotic Initiation Factor 4E, 1988, J Biol Chem 263(33):17229–32.

de la Luna, Molecular cloning and sequencing of influenza virus A/Victoria/3/75 polymerase genes etc, 1989, Virus Res 13:143–55.

Perales, Mutational Analysis Identifies Functional Domains in the Influenza A virus PB2 Polymerase Subunit, Mar. 1996, J Virol. 70(3):1678–86.

Hassett, Targeted construction of temperature–sensitive mutations in vaccinia virus by replacing clustered charged residues with alanine, 1994, Proc Natl Acad Sci 91:4554–58.

Wiskerchen, Identification and characterization of a Temperature Sensitive Mutant of Human Immunodeficiency Virus Type 1 by Alanine Scanning Mutagenesis of the Integrase Gene, Jan. 1995, J Virol 69(1):597–601.

Diamond, Clustered Charged–to–alanine Mutagenesis of Poliovirus RNA–Dependent RNA Polymerase Yields Multiple Temperature–Sensitive Mutants Defective in RNA Synthesis, 1994, J Virol 68(2):863–876.

Plotch, A unique Cap(m7GpppXm)–Dependent Influenza Virion Endonuclease Cleaves Capped RNAs to Generate the Primers That Initiate Viral RNA Transcription, 1981, Cell 23:847–58.

Powers, Reduced Infectivity of Cold–Adapted Influenza a H1N1 Viruses in the Elderly etc, 1992, J Am Ger Soc 40:163–67.

Li, Electroporation of influenza virus ribonucleoprotein complexes for rescue of the nucleoprotein ad natrix genes, 1995, Virus Res 37:153–61.

Soneberg, Cap–Binding Proteins of Eukaryotic Messenger RNA etc, 1988, Prog Nucleic Acid Res Mol Biol 35:173–207.

*Primary Examiner*—Hankyel Park
*Attorney, Agent, or Firm*—Luann Cserr; Tracy Dunn

[57] ABSTRACT

Recombinant PB2 tryptophan variant influenza viruses, RNA, cDNA and vectors are provided. Also provided are immunogenic compositions containing the variant viruses, methods of producing such viruses and methods for the prophylactic treatment of influenza in humans.

21 Claims, No Drawings

RECOMBINANT TRYPTOPHAN MUTANTS OF INFLUENZA

FIELD OF THE INVENTION

This invention relates to influenza virus immunogenic compositions and methods of producing such compositions. More specifically, this invention relates to influenza virus immunogenic compositions having discreet, specifically engineered mutations in the native PB2 polymerase RNA sequence of influenza resulting in the deletion of, and/or substitution of, at least one of the native tryptophan amino acid residues in the PB2 protein.

BACKGROUND

Influenza is an enveloped, single-stranded, negative-sense RNA virus that causes serious respiratory ailments throughout the world. It is the only member of the Orthomyxoviridae family and has been subgrouped into three types, A, B and C.

Influenza virions consist of an internal ribonucleoprotein core containing the single-stranded RNA genome and an outer lipoprotein envelope lined inside by a matrix (hereinafter "M1") protein. The segmented genome of influenza A consists of eight molecules of linear, negative polarity, single-stranded RNA sequences that encode ten polypeptides. Segment 1 is 2341 nucleotides in length and encodes PB2, a 759 amino acid polypeptide which is one of the three proteins which comprise the RNA-dependent RNA polymerase complex. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively. Segment 4 of the genome consists of a 1778 nucleotide sequence encoding a 566 amino acid hemagglutin (HA) surface glycoprotein which projects from the lipoprotein envelope and mediates attachment to and entry into cells. Segment 5 consists of 1565 nucleotides encoding a 498 amino acid nucleoprotein (NP) protein that forms the nucleocapsid. Segment 6 consists of a 1413 nucleotide sequence encoding a 454 amino acid neuraminidase (NA) envelope glycoprotein. Segment 7 consists of a 1027 nucleotide sequence encoding a 252 amino acid M1 protein, and a 96 amino acid M2 protein, which is translated from a spliced variant of the M RNA. Segment 8 consists of a 890 nucleotide sequence encoding two nonstructural proteins, NS1 and NS2, composed of 230 and 121 amino acids respectively, whose function is not well defined. NS2 is translated from a spliced variant of the NS RNA.

The segmented genome of influenza B consists of eight molecules of linear, negative polarity, single-stranded RNA sequences that encode eleven polypeptides. Segment 2 is 2396 nucleotides in length and encodes PB2, a 770 amino acid polypeptide which is one of the three RNA-dependent RNA polymerase proteins. The remaining two influenza B polymerase proteins, PB1, a 752 amino acid polypeptide, and PA, a 725 amino acid polypeptide, are encoded by a 2386 nucleotide sequence and a 2304 nucleotide sequence (segments 1 and 3), respectively. Segment 4 of the genome consists of a 1882 nucleotide sequence encoding a 584 amino acid HA surface glycoprotein which projects from the lipoprotein envelope and mediates attachment to cells and membrane fusion. Segment 5 consists of 1839–1841 nucleotides encoding a 560 amino acid NP protein that forms the nucleocapsid. Segment 6 consists of a 1454 nucleotide sequence encoding a 466 amino acid NA envelope glycoprotein and a 100 amino acid NB protein, a nonstructural protein whose function is unknown. Segment 7 consists of a 1191 nucleotide sequence encoding a 248 amino acid M1 protein and a 195 amino acid BM2 protein which is translated from a separate reading frame. Segment 8 consists of a 1096 nucleotide sequence encoding nonstructural proteins NS1 and NS2, composed of 281 and 122 amino acids respectively, whose functions are not well defined. NS2 is translated from a spliced variant of the NS RNA.

The segmented genome of influenza C consists of seven molecules of linear, negative polarity, single-stranded RNA sequences that encode eight polypeptides. Segment 1 is 2365 nucleotides in length and encodes PB2, a 774 amino acid polypeptide which is one of the three RNA-dependent RNA polymerase proteins. The remaining two polymerase proteins, PB1, a 754 amino acid polypeptide, and PA, a 709 amino acid polypeptide, are encoded by a 2363 nucleotide sequence and a 2183 nucleotide sequence (segments 2 and 3), respectively. Segment 4 of the genome consists of a 2074 nucleotide sequence encoding a 655 amino acid hemagglutinin-esterase surface glycoprotein which projects from the lipoprotein envelope and mediates attachment to cells, fusion, and has receptor-destroying activities. Segment 5 consists of a 1809 nucleotide sequence encoding a 565 amino acid NP protein that forms the nucleocapsid. Segment 6 consists of a 1180 nucleotide sequence encoding a 374 amino acid matrix (M) protein. Segment 7 consists of a 934 nucleotide sequence encoding a 286 amino acid NS 1 protein, and a 122 amino acid NS2 protein, which is translated from a spliced variant of the NS RNA.

To infect a cell influenza HA protein adsorbs to sialyloligosaccharide molecules in cell membrane glycoproteins and glycolipids. Following endocytosis of the virion, a conformational change in the HA molecule occurs within the cellular endosome that facilitates membrane fusion and triggers uncoating. The nucleocapsid migrates to the nucleus where viral mRNA is transcribed as the essential initial event in infection. Transcription and replication of influenza RNA take place in the nucleus of infected cells and assembly into virions occurs by budding out of or through the plasma membrane. Viruses can reassort genes during mixed infections.

Replication of influenza virus RNAs is dependent on four viral gene products: PB1, PB2, PA, and NP. The three polymerase proteins, PB1, PB2, and PA, form a trimolecular complex in the nuclei of infected cells. Some specific functions have been ascribed to the individual polypeptides. PB1 appears to be primarily involved in the enzymatic polymerization process, i.e. the elongation step. It shares regions of amino acid sequence similarity with other RNA-dependent RNA polymerase proteins. The precise function of PA is unknown. The PB2 protein binds to the 5'-terminal cap structure present on host cell mRNAs; the mRNAs are then cleaved, producing a capped 9 to 15-mer oligoribonucleotide which serves as a primer for transcription of influenza mRNAs. See Plotch, *Cell* 23: 847–58 (1981). Thus, it is suspected that PB2 has cap-binding and endonuclease activities. While it is thought that PB2 is not absolutely required for replication of viral RNA, mRNAs transcribed from viral template in cells expressing only PB1, PA, and NP are uncapped and thus cannot be translated. See Nakagawa, *J Virol* 69:728–33 (1995). Transcripts terminate at sites 15–22 bases from the ends of their templates, where oligo(U) sequences act as signals for the template-independent addition of poly(A) tracts. At a later stage of infection, instead of making mRNAs, the polymerase proteins PB1, PB2 and PA are used to make new viral RNA genomes. The polymerase complex transcribes cRNA, which then serves as template for production of more vRNA. The plus-stranded cRNA copies differ from the plus-stranded mRNA transcripts by lacking capped and methylated 5'-termini. Also, they are not truncated or polyadenylated at the 3' termini. Thus, the cRNAs are coterminal with their negative strand templates and contain all the genetic information in each genomic segment in the complementary form.

The negative strand genomes (vRNAs) and antigenomes (cRNAs) are always encapsidated by viral nucleocapsid proteins; the only unencapsidated RNA species are virus mRNAs. Nucleocapsid assembly appears to take place in the nucleus. The virus matures by budding from the apical surface of the cell incorporating the M1 protein on the cytoplasmic side or inner surface of the budding envelope. The HA and NA glycoproteins are incorporated into the lipid envelope. In permissive cells, HA is post-translationally cleaved, but the two resulting chains remain associated by disulfide bonds.

Efforts to produce immunogenic compositions against influenza have taken two paths. Inactive vaccines, which cannot replicate in the host, can be either chemically inactivated whole virus or viral subunit proteins. Both inactivated and subunit virus vaccines are available for influenza. These vaccines contain the HA and NA surface proteins as antigens which give rise to the immune response upon administration to the host. For reasons which are incompletely understood, subunit vaccines have exhibited an efficacy of only 60% to 80% against influenza disease. Inactivated whole virus vaccines are administered intramuscularly and primarily stimulate a humoral immune response, whereas live attenuated vaccines also stimulate local mucosal immunity. The latter form of immunity is more effective since it is present in the upper respiratory tract where a wild-type virus would first be encountered. Also, inactivated vaccines typically have reduced ability to induce cytotoxic T cell responses, and can sometimes cause delayed hypersensitivity reactions. Guillain-Barre syndrome has been associated with the inactivated influenza A "swine flu" vaccine. See, Schonberger, *Ann Neurol* 9(supp):31–38 (1981).

Live attenuated viruses can be employed in immunogenic compositions and are typically successful at inducing the required protective response in the host. Live attenuated influenza viruses are capable of limited replication in the host, thus stimulating a protective immune response, but without causing disease. In making such vaccine compositions, the HA and NA RNA sequences of the attenuated "master donor" virus are replaced with HA and NA RNA sequences from circulating influenza strains. Such viruses are termed reassortant viruses. Previously, such master donor viruses have been generated by multiple passage through an unnatural host such as embryonated chicken eggs, by reassortment of genes between human and avian influenza viruses, by successive passage through an unnatural host at increasingly lower temperatures, or by random mutagenesis via chemical methods and selection of conditional mutants. These methods can result in the loss of pathogenicity while retaining immunogenicity. However, the identity of the genetic mutations generated as described above are unknown a priori and when the mutant "master donor" virus is selected as a vaccine candidate. If such mutations are limited to one or two nucleotide changes, the virus composition could ultimately "revert" or back mutate in the host and thus regain its original pathogenic phenotype. However, one of these methods, successive passage at increasingly lower temperatures, has given rise to a virus (the "cold-adapted" strain derived from A/Ann Arbor/6/60) with multiple mutations that has been shown to be genetically stable. See Murphy, *Inf Dis In Clin Practice* 2:174–81 (1993). This cold-adapted vaccine may be highly effective in children and younger adults but appears to be less immunogenic in the elderly population. See Powers, *J Am Ger Soc* 40:163–67(1992).

Temperature sensitive (ts) mutants of influenza, generated by chemical mutagenesis or identified by screening for spontaneous mutants have been described. Such mutants are unable to replicate in the lower respiratory tract of infected animals and often replicate in the upper respiratory tract to a lower level than wild-type virus. One of these mutants, ts1 A2, was shown to have many of the desired characteristics of a live attenuated influenza vaccine. See Murphy and Chanock, *Genetic Variation Among Influenza Viruses*, pps 601–15, Nayak, D.ed, Academic Press, N.Y. (1981) and Murphy, *Phil Trans R Soc Lon B* 288:401–15(1980). The ts1A2 strain was found to contain temperature sensitive lesions in both PB1 and PB2, and exhibited the desired level of attenuation, but was genetically unstable and reverted to a virulent state after replication in a seronegative young vaccinee. See Murphy, *Ann NY Acad Sci* 354:17–82 (1980) and Tolpin, *Infection and Immunity* 36:64–50 (1982). Other ts mutants of influenza are known, the nucleotide sequences of their PB2 genes and the locations of the ts lesions in those genes have been determined. See Lawson, *Virology* 191:506–10(1992).

An alternate method of creating a live attenuated virus is by employing the techniques of "reverse genetics". See Enami, *Proc Natl Acad Sci* 87:3802–05(1990), Enami and Palese, *J Virol* 65:2711–13(1991) and Luytjes, *Cell* 59:1107–13 (1989). In this process, modified vRNA▲like transcripts are transcribed in vitro from cDNA constructs in the presence of purified NP, PB1, PB2, and PA proteins. The resulting synthetic RNP is then transfected into cells previously infected with an influenza helper virus. This helper virus usually has a conditional growth defect, such as host range restriction or temperature sensitivity, which allows the subsequent selection of transfectant viruses. For example, host-range helper viruses have been successfully used to rescue synthetic NA and PB2 genes. See Enami, supra, and Subbarao, *J Virol* 67:7223–28 (1993). Antibody selection can also be used to select transfectants in the case of the HA and NA genes. Using antibody selection techniques, the surface HA glycoprotein gene has been transfected and rescued into influenza A virus. See, Horimoto and Kawaoka, *J Virol* 68:3120–28 (1994) and Li, *J Virol* 66:399–404 (1992). A modified HA gene has also been transfected and rescued into influenza B virus. See, Barclay and Palese, *J Virol* 69:1275–79 (1995). The M gene (see, Yasuda, *J Virol* 68:8141–46 (1994)), and the NP gene (see Li, *Virus Res* 37:153–61(1995), have also been rescued using the techniques of reverse genetics.

Given the possibility of using reverse genetics to engineer specific mutations into the genome of influenza, it should be possible to create a virus strain with mutations that are less likely to revert and thus exhibit the desired property of genetic stability. This may be accomplished by introducing new codons which would require more than one nucleotide within the codon to mutate in order to encode the wild-type amino acid, by mutating sites which are less likely to be suppressed extragenically, by introducing multiple, independently-acting mutations in one or more genes, or by a combination of these approaches.

Studies with eukaryotic cellular cap-binding proteins have been largely confined to the eukaryotic translation initiation factor, eIF-4E. This 24 kilodalton (kD) protein binds to the cap structures on mRNAs and enables translation initiation in concert with a bevy of other eIFs. See Sonenberg, *Prog Nucleic Acid Res Mol Biol* 35:173–207 (1988). Although the amino acids of the eIF-4E protein that interact directly with the cap structure have not been identified, biophysical studies have suggested the involvement of tryptophan residues in the eIF-4E protein. See Ishida, *Biochem and Biophys Res Comm* 115:849–54(1983). Site directed mutagenesis of tryptophan residues in the eIF-4E protein of *Saccharomyces cerevisiae* followed by assays for cap-binding suggested that two of the eight tryptophan residues present in the protein, those at the amino and/or carboxyl termini, might play a role in cap-recognition, while mutagenesis of certain other tryptophan residues resulted in mutated protein that still exhibited efficient cap-binding but reduced cross-linking ability relative to the wild-type protein. See Altmann, *J Biol Chem* 263:17229–32(1988).

The PB2 polypeptide has been shown to have cap-binding activity by cross-linking studies to cap analogs. By comparing the amino acid sequence of PB2 with those of the human and yeast cap-binding proteins, it has been theorized that the cap-binding activity in PB2 is located in two regions of the polypeptide sequence: amino acids 552–565 and amino acids 633–650. See de la Luna, *Virus Res* 13:143–56(1989). It has been speculated that one PB2 mutant, apparently having an inserted amino acid at position 299, is suspected of affecting cap binding or cap-dependent endonuclease activity. See Perales, *J Virol* 70:1678–86(1995). These authors also speculate that certain surrounding amino acids, presumably at positions 236, 469 and 480, define a region involved in cap binding in PB2. Id. at 1685.

SUMMARY OF THE INVENTION

In contrast to prior studies, we have identified one region, spanning PB2 amino acid residues 537–575, as most likely to contain the cap-binding activity. This region contains four tryptophan residues, at amino acid positions 537, 552, 557, and 564 (counting from the N-terminal MET, as residue 1). Additionally, we have found that modification of one or more of these tryptophan residues in the native PB2 protein of influenza, by deletion, or by substitution or replacement with a non-native residue, alone or in combination with other known PB2 ts lesions, results in the exhibition of attenuation of virulence and temperature sensitivity in influenza virus.

Accordingly, in one aspect the invention comprises novel PB2 tryptophan variant polypeptide sequences and RNA sequences encoding PB2 tryptophan variant polypeptides, which, when incorporated into influenza viral master donor viruses, cause such viruses to exhibit an attenuated and temperature sensitive phenotype. The PB2 tryptophan variant polypeptides of this invention comprise variant or modified PB2 amino acid sequences in which at least one and up to four of the tryptophan residues of wild-type (i.e., native) influenza PB2 sequences believed to be involved in cap-binding are modified by deletion or by replacement or substitution with non-native amino acids. The PB2 tryptophan variant polypeptides of this invention comprise variant or modified PB2 sequences which, in addition, may contain one or more amino acid substitutions known to be responsible for temperature-sensitivity. A number of such "ts" mutants of human influenza A/Udorn/307/72 virus are known. A summary of the nucleotide and deduced amino acid sequence changes in the PB2 RNA sequences of certain of these ts mutants is disclosed in Lawson, *Virus Res* 191:506–10(1992) and in PCT Patent Publication WO 95/08634 published Mar. 30 1995, which are herein incorporated by reference. Of particular interest are A/Udorn/307/72 mutants in which the native E at position 65 is replaced with G (using the accepted one-letter abbreviations for amino acids) and in which the native P at position 112 is replaced with S in PB2. Other ts mutations encompassed by this invention include that found in the PB2 gene of the cold adapted strain of human influenza A/AA/6/60, in which the native N is replaced with S at amino acid position 265.

The invention also comprises RNA and cDNA sequences which encode the PB2 tryptophan variant polypeptides of the invention.

The PB2 tryptophan variant RNA sequences of this invention can be rescued into influenza genomes to create influenza master donor virus strains containing the specific mutations desired using the techniques of reverse genetics. Thus, in another aspect the invention comprises recombinant influenza viruses containing such novel PB2 tryptophan variant RNA and polypeptide sequences. These recombinant influenza viruses display attenuated growth characteristics in cultured cells and/or live hosts and are useful as master donor viruses in the preparation of influenza virus reassortants and immunogenic compositions for the prophylactic treatment of humans for influenza infection. To make such recombinant influenza viruses, permissive host cells are infected with a helper virus and transfected with a synthetic RNP complex. The synthetic RNP complex is transcribed in vitro from DNA that encodes the mutated RNA sequence and packaged into ribonucleoprotein (RNP) before transfection. Viral progeny resulting from the transfection includes virus that has incorporated the mutated, transfected RNA sequence into viral particles. Transfectant viruses recovered from the cells that have incorporated the mutated, transfected sequence are then selected from the mixture of transfectant and helper virus, exploiting a phenotypic difference between the two viruses. These transfectant viruses so selected comprise the recombinant influenza viruses of the invention. In such embodiment, the modified tryptophan variant PB2 sequence will contain one or more deletions, replacements or substitutions of the tryptophan amino acid residues giving rise to attenuating phenotypes.

In yet another aspect the invention comprises a method of producing modifications in an influenza genome comprising introducing a recombinant, negative strand RNA template encoding a PB2 tryptophan variant polypeptide into cells infected with a helper virus capable of producing influenza virus RNA segments. One helper virus which can be employed is capable of growth in avian cells but not in mammalian cells. More specifically for example, Madin-Darby bovine kidney (MDBK) or primary chick kidney (PCK) cells can be infected with a host-range mutant of influenza containing the PB2 gene of an avian virus. See Clements, *J Clin Microbiol* 30:655–662 (1992). Synthetic PB2 RNP is then prepared by in vitro transcription of a cDNA template encoding the mutated, vRNA-sense, PB2 RNA in the presence of purified RNP proteins. The cDNA must encode a PB2 protein which, when rescued into the helper virus, allow it to form plaques in mammalian cells. The resulting RNP is introduced into the infected MDBK or PCK cells, the cells incubated and the medium harvested and used to infect MDCK cells.

In yet another aspect, the invention comprises a reassortant virus including RNA sequences encoding the HA and NA glycoproteins derived from a wide-type epidemic strain of influenza virus, and the remaining RNA sequences derived from the transfectant virus. The wide-type epidemic virus is a circulating strain of influenza virus against which immunity is desired. The transfectant virus is the attenuated master donor, i.e. recombinant influenza virus of the invention which contains attenuating mutations in one or more of the native tryptophan residues in the PB2 sequences of the invention as disclosed herein which can be created and tested for attenuation following the methods described herein. The most reproducible way to generate a suitably attenuated vaccine virus is to retain all six of the internal protein RNA segments (PB1, PB2, PA, NP, M, and NS) of the master donor; however, it may also be possible to have fewer master donor segments in the vaccine virus but still maintain an appropriate level of attenuation, and genetic stability.

In yet another aspect, the invention comprises immunogenic pharmaceutical compositions containing an immunogenically-inducing effective amount of an influenza virus variant in admixture with a pharmaceutically acceptable carrier or solution.

In yet another aspect the invention comprises a method for the prophylactic treatment of a patient comprising administering an immunogenically-inducing effective amount of an immunogenic pharmaceutical composition of the invention to such patient. By "immunogenically-inducing" we mean an amount sufficient for stimulating in a mammal the production of protective antibodies to influenza. Such an amount may stimulate antibody production locally and/or systemically, thereby preventing infection or the disease caused by such infection. Preferably, the patient is a human patient.

DETAILED DESCRIPTION OF THE INVENTION

In this disclosure, reference is made to the common amino acids using the conventional single-letter symbols.

The modification of tryptophan residues in the influenza virus native PB2 protein or polypeptide (which terms "protein" and "polypeptide" are used interchangeably herein) results in the exhibition of attenuation, and surprisingly, temperature sensitivity in the virus. Such modification encompasses deletion of the native tryptophan residue, or substitution or replacement of the native tryptophan amino acid residue with a non-native amino acid residue. Preferred amino acids for replacement or substitution include phenylalanine, tyrosine and histidine. Especially preferred is phenylalanine. Ten tryptophan amino acid residues were identified in the native influenza A virus A/LA/2/87 PB2 protein. These are located at amino acids 49, 78, 98, 99, 240, 449, 537, 552, 557, and 564, using the conventional numbering counting from the N-terminal MET residue as 1.

Analysis of amino acid sequences of the PB2 proteins from numerous other influenza A strains identified the corresponding tryptophan residues in those strains. Such influenza A strains include A/Memphis/8/88, A/Chile/1/83, A/Kiev/59/79, A/Udorn/307/72, A/NT/60/68, A/Korea/426/68, A/Great Lakes/0389/65, A/Ann Arbor/6/60, A/Leningrad/13/57, A/Singapore/1/57, A/PR/8/34 and A/WSN/33. Their sequences are available from GenBank and viral stock may be available from the American Type Culture Collection, Rockville, Md. or are otherwise publicly available. Thus, although the A/LA/2/87 strain was used in the examples, any of the foregoing strains could equally have been used. In addition, analyses for tryptophan residues in the PB2 proteins of influenza B and/or C virus could be readily performed in accordance with the teachings of this invention to create PB2 tryptophan variant proteins and live recombinant influenza B and influenza C viruses in an manner analogous to that demonstrated here for influenza A. For example, tryptophan residues corresponding to positions 49, 98, 99, 240, 449, 537 and 552 in influenza A have been found in two influenza B strains, B/AA/1/66 and B/NY/1/93; those at positions 49, 78, 99 and 240 have also been found in the PB2 protein of influenza C virus C/JJ/50. See Yamashita, *Virology* 171: 458–66 (1989).

Tryptophan residues can be modified following the teachings here to create attenuated, temperature sensitive recombinant influenza viruses. Such attenuated, temperature sensitive recombinant influenza viruses include those containing the PB2 tryptophan variant amino acid sequences, and their encoding RNA or cDNA sequences, which are responsible for the exhibited attenuation and temperature sensitivity.

Accordingly, this invention discloses and describes novel RNA and corresponding cDNA sequences encoding influenza PB2 tryptophan variant proteins. The proteins of this invention comprise variant or modified influenza PB2 sequences in which at least one and up to four of the tryptophan residues of wild-type (i.e., native) influenza PB2 sequences involved in cap-binding are modified by deletion or by replacement or substitution with other amino acids. Phenylalanine is a preferred replacement amino acid. Other preferred amino acids include tyrosine and histidine. The preferred tryptophan amino acid residues for deletion, substitution or replacement are those residues involved in the cap-binding activity of the PB2 protein. In influenza A, those amino acid residues are believed to be the native tryptophan amino acid residues at positions 537, 552, 557 and 564. The words variant, modified and mutant or mutated are used interchangeably herein. The novel RNA and corresponding cDNA sequences encoding influenza PB2 tryptophan variant proteins may also comprise variant or modified influenza PB2 sequences in which the PB2 ts mutations described in detail in Lawson, *Virus Res* 191:506–10(1992) and in PCT Patent Publication WO 95/08634 published Mar. 30, 1995 are included. Specifically, such influenza A PB2 polypeptide sequences containing mutations at amino acid positions 65, 100, 112, 174, 298, 310, 386, 391, 556, 658, 265, 417 and 512 ("ts amino acids"), and their corresponding mutated codons, in combination with the deletion, replacement or substitution of from one to four PB2 tryptophan residues believed to be involved in cap-binding, also comprise the novel RNA, cDNA and polypeptide sequences of the invention. Mutant PB2 polypeptide sequences containing deletions, substitutions or replacements at ts amino acids 65, 112 and 265 and at from one to four tryptophan residues are preferred. Mutant PB2 polypeptide sequences containing deletions, substitutions or replacements at ts amino acids 65, 112 and 265 and tryptophan residues 552, 557 and 564 are most preferred; and substitution or replacement of those ts amino acids and those tryptophan residues is especially preferred.

Such proteins, when incorporated into influenza viruses to create master donor strains of influenza, result in the creation of attenuated and temperature sensitive mutants useful in the preparation of immunogenic compositions and in the prophylactic treatment of influenza.

The influenza PB2 tryptophan variant proteins (i.e., the influenza PB2 proteins containing one or more deleted, replaced or substituted tryptophan amino acid residues and optionally containing one or more ts deletion, replacement or substitution) of this invention can be incorporated into influenza viruses by employing known genetic reassortment or reverse genetic methods. In reverse genetic methods, the native influenza PB2 nucleotide sequence is replaced with a synthetic gene synthesized in vitro from cDNA. The cDNA has at least one of the codons encoding at least one of the native tryptophan amino acid residues believed to be involved in cap-binding either deleted, or replaced or substituted with nucleotides encoding a non-native amino acid residue. Optionally, the cDNA also has at least one of the codons encoding at least one of the native amino acid residues known to be responsible for the ts phenotype, preferably residues 65 and/or 112 of A/Udorn/307/72 and/or 265 of A/AA/6/60(ca), either deleted or replaced or substituted with nucleotides encoding a non-native amino acid residue. Preferably, the codons should be modified such that reversion to the wild-type amino acid is less likely, by replacing at least two of the nucleotides with non-native nucleotides. Helper virus infected cells are transfected with the synthetic influenza PB2 tryptophan variant RNA sequence. The live virus containing the synthetic influenza PB2 tryptophan variant RNA and amino acid sequence can serve as a master donor virus, which, when combined with the wild-type HA and/or NA gene of epidemic (i.e., currently circulating virulent) influenza strains, will result in the production of reassortant influenza viruses ("6:2 reassortants") which can be used as immunogenic compositions in the prophylactic treatment of influenza in human. The 6:2 reassortant viruses will thus be composed of six genes derived from the master donor strain containing the synthetic sequence or sequences and the HA and NA genes derived from a currently circulating virulent strain of influenza. The method of preparing a 6:2 influenza reassortant virus comprises infecting a cell with the attenuated master donor strain and with a currently-circulating virulent influenza A virus and selecting the reassortant virus by inhibiting the replication of viruses containing the HA and NA genes of the master donor strain by incubation with an antibody reactive with those proteins. Alternatively, reverse genetics techniques can be used to transfect cells with the HA and NA genes from an epidemic strain. The cells are then infected with the master donor strain and 6:2 reassortants selected by antibody mediated selection as described above.

For example, primary chick kidney (PCK) or MDBK cell monolayers are infected with helper virus at a multiplicity of infection (moi) of 1–10 for 1 hour. RNA encoding one or more of the tryptophan variant PB2 proteins of the invention is transfected into the infected cells using the techniques described in Luytjes, supra, Enami and Palese, supra and Enami, supra optionally as modified in Example 4 below. The transcription reaction contains linearized plasmid, each of the deoxyribonucleotides, T3 RNA polymerase and ribonucleoprotein prepared from virus grown in the allantoic cavities of embryonated eggs according to the methods of Parvin, supra. The mixture is incubated at 37° C. for 45 minutes, resulting in the production of RNA transcripts which are concurrently packaged into RNP complexes. The addition of DNase then eliminates the plasmid and the mixture is introduced into the PCK or MDBK cells, which have been infected with the helper virus and treated with DEAE Dextran. Alternatively, the mixture is introduced into the infected cells by electroporation. Cultures are maintained at the appropriate temperature (e.g. 34° C.) and are harvested about 16–22 hours later. Cell debris is pelleted and the supernatant containing the virus is plaqued on appropriate mammalian cells, for example MDCK cells. The progeny of the plaqued virus can go through subsequent additional plaque passages and is then amplified in the allantoic cavities of embryonated eggs.

More specifically, a host-range mutant of influenza virus A/LA/2/87 has been described. This helper virus contains the PB2 gene derived from the avian virus, A/Mallard/New York/6750/78, and is able to grow productively in avian cells such as PCK cells, but cannot form plaques in mammalian cells such as MDCK. See Clements, *J Clin Microbiol* 30:655–62 (1992). Replacement of the Mallard PB2 gene in the helper virus with a transfected, mammalian PB2 sequence allows the virus to plaque in MDCK cells. See Subbarao, *J Virol* 67:7223–28 (1993). In this way specific alterations in the nucleotide sequence of the PB2 gene can be introduced, by transfecting synthetic RNAs derived from cDNAs of the mammalian PB2 sequence bearing site-directed mutations. The recombinant variant influenza virus so produced will exhibit temperature sensitivity, thereby enabling it to be employed as the master donor strain in the construction of live, attenuated immunogenic compositions for prophylactic administration in humans.

Standard methods may be employed for propagating the recombinant influenza viruses of the invention. Viral stocks can be plaque-purified in primary or established cell cultures, for example, primary bovine or chick kidney cells or MDCK cells. Plaque-purified virus can be further propagated in such cell lines. The cells are cultured typically on plastic tissue culture plates and virus is typically inoculated at a moi of 0.001 to 0.1 and incubated for 2–3 days. Virus stock can alternatively be inoculated into the allantoic cavity of 10–12 day embryonated chicken eggs and incubated for 2–3 days at 33–37° C.

Testing for attenuation of the recombinant influenza viruses of the invention can be accomplished employing well established in vitro and in vivo assays. In the in vitro assay, the recombinant virus is tested for the presence of the temperature sensitive phenotype, as described in Example 6 below. Ability to replicate in the respiratory tract of mice can be determined as described in Example 7 below. In vivo reactogenicity of the recombinant influenza viruses can be determined as described in Example 8 below. Phenotypic stability of the recombinant influenza viruses can be determined as described in Example 9 below.

Such recombinant modified, variant influenza viruses can also be used in genetic complementation analysis, to map ts lesions of other viruses, and in the functional analysis of the role of PB2 in the virus life cycle.

The modified PB2 proteins of the invention can be expressed recombinantly in different types of cells using the appropriate expression control systems, as is well known in the art, to test protein functionality. The construction of suitable vectors containing the nucleic acids sequences of the invention is likewise well known in the art, as are hybridization assays in which such sequences may be employed. See for example, U.S. Pat. No. 4,356,270 issued to Itakura, U.S. Pat. No. 4,431,739 issued to Riggs and U.S. Pat. No. 4,440,859 issued to Rutter. Other exemplary host cells, promoters, selectable markers and techniques are also disclosed in U.S. Pat. No. 5,122,469 issued to Mather, U.S. Pat. Nos. 4,399,216 and 4,634,665 issued to Axel, U.S. Pat. No. 4,713,339 issued to Levinson, U.S. Pat. No. 4,656,134 issued to Ringold, U.S. Pat. No. 4,822,736 issued to Kellems and 4,874,702 issued to Fiers.

The construction of suitable vectors containing the nucleic acid sequences of the invention is accomplished using conventional ligation and restriction techniques now well known in the art. Site specific cleavage is performed by treatment with suitable restriction enzyme(s) under standard conditions, the particulars of which are typically specified by the restriction enzyme manufacturer. Polyacrylamide gel or agarose gel electrophoresis may be performed to size separate the cleaved fragments using standard techniques. Synthetic oligonucleotides can be made using for example, the diethyphosphoamidite method known in the art. Ligations can be performed using T4 DNA ligase under standard conditions and temperatures, and correct ligations confirmed by transforming E. coli with the ligation mixture. Successful transformants are selected by ampicillin, tetracycline or other antibiotic resistance or using other markers as are known in the art.

Such recombinant techniques are fully explained in the literature. See, e.g., Sambrook, *Molecular Cloning: A Laboratory Manual*, 2d ed. (1989); *DNA Cloning*, Vol. I and II, D. N. Glover, ed., 1985; *Oligonucleotide Synthesis*, M. J. Gait, ed., 1984; *Nucleic Acid Hybridization*, B. D. Hames, ed., 1984; *Transcription and Translation*, B. D. Hames, ed., 1984; *Animal Cell Culture*, R. I. Freshney, ed., 1986; B. Perbal, *A Practical Guide to Molecular Cloning* (1984); *Gene Transfer Vectors for Mammalian Cells*, J. H. Miller, ed., 1987, Cold Spring Harbor Laboratory; Scopes, *Protein Purification: Principles and Practice*, 2d ed, Springer-Verlag, New York, 1986 and *Handbook of Experimental Immunology*, Vols I–IV, D. M. Weired, ed., 1986. All such publications mentioned herein are incorporated by reference for the substance of what they disclose.

The live recombinant influenza virus variants of the invention may be employed in immunogenic compositions for preventing infection by an influenza virus or the disease state brought about by such infection. To make such immunogenic compositions, cultured cells are co-infected with the live recombinant influenza variant (i.e., the master donor) and an epidemic wild-type strain. Reassortant viruses are harvested and tested for the presence of the mutation in the native tryptophan residue. Reassortants containing the wild-type HA and/or NA proteins can be selected by exposure to antisera against the surface epitopes encoded by the HA and/or NA proteins from the donor virus. Resultant viral progeny containing the mutated sequences of the invention and the HA and/or NA sequences from the wild-type epidemic influenza strains are used in the preparation of immunogenic compositions. Such immunogenic compositions comprise an immunogenically-inducing effective amount of a recombinant influenza virus variant of the present invention in admixture with a pharmaceutically acceptable carrier or solution. An exemplary pharmaceutically acceptable carrier is saline solution. The composition can be systemically administered, preferably subcutaneously or intramuscularly, in the form of an acceptable subcutaneous or intramuscular solution. More preferably, the composition can be administered intranasally, either by drops, large particle aerosol (greater than 10 microns), or spray into the upper respiratory tract. The preparation of such solutions, having due regard to pH, isotonicity, stability and the like is within the skill in the art. The dosage regimen will be determined by the attending physician considering various factors known to modify the action of drugs such as for example, age, physical condition, body weight, sex, diet, time of administration and other clinical factors. Exemplary dosages range from about 1 to about 1000 $HID_{50}$ (human infectious dose) of the virus.

In practicing the method of prophylactic treatment of this invention, an immunologically-inducing effective amount of an immunogenic composition of the invention is administered to a human patient in need of prophylactic treatment. An immunologically inducing effective amount of a composition of this invention is contemplated to be in the range of about 1–1000 $HID_{50}$, i.e., about $10^5$–$10^8$ pfu (plaque forming units) per dose administered. The number of doses administered may vary, depending on the above-mentioned factors. The route of delivery will preferably be via nasal administration into the upper respiratory tract of the patient.

The invention is further described in the following examples, which are intended to illustrate the invention without limiting its scope.

EXAMPLE 1 cDNA Cloning of A/LA/2/87 Gene

Madin-Darby canine kidney (MDCK) and Madin-Darby bovine kidney (MDBK) cells were obtained from the American Type Culture Collection (ATCC, Rockville, Md.) and grown in Eagle's Modified Essential Medium (EMEM; JRH Biosciences, Lenexa, Kans.) supplemented with 10% fetal bovine serum (JRH), 2 mM L-glutamine (JRH), 100 units/ml penicillin and 0.1 mg/ml streptomycin (Sigma, St. Louis, Mo.), at 37° C. in 5% $CO_2$. Influenza virus A/LA/2/87 (H3N2) was obtained from Dr. L. Potash (DynCorp/PRI, Rockville, Md.), passaged once in MDCK cells at 37° C., then amplified in the allantoic cavity of 10–12 day old, Standard quality, specific pathogen-free (SPF) embryonated chicken eggs (SPAFAS, Norwich, Conn.) at 35° C. as described in Barrett, *Growth, Purification and Titration of Influenza Viruses*, p.119–150, B. W. J. Mahy, ed., IRL Press, Oxford, England (1985).

Allantoic fluid from eggs infected with A/LA/2/87 virus was removed and concentrated by centrifugation at 15,000 rpm in an SW28 rotor for 90 minutes at 4° C., then purified by centrifugation on a sucrose step gradient (12–60% sucrose in phosphate-buffered saline) in four 12% steps at 27,000 rpm in an SW28 rotor for 75 minutes at 4° C. Banded virions were disrupted with 1% NP-40. Viral RNA (vRNA) was then extracted, first by treatment with 0.5 mg/ml proteinase K (PK; Amresco, Solon, Ohio) in the presence of 1% sodium dodecyl sulfate (SDS), 50 mM tris (hydroxymethyl) aminomethyl hydrochloride (Tris), pH 7.5, 100 mM NaCl and 1 mM ethylene-diamine-tetra-acetate (EDTA), at 37° C. for 1 hour and then by three successive treatments with an equal volume of phenol/chloroform, and precipitated with 2.5 volumes of ethanol.

After chilling at −20° C. for 1 hour, the RNA containing precipitate was pelleted by centrifugation in an Eppendorf microcentrifuge at 14,000 rpm for 20 minutes, washed with 80% ethanol, dried and resuspended in diethyl pyrocarbonate (DEPC)-treated water to a final concentration of 0.5 mg/ml. Approximately 1 $\mu$g of vRNA was hybridized with oligonucleotide PB2003, an oligonucleotide complimentary to the 24 3'-terminal nucleotides of the PB2 gene, based on the sequence of the A/Memphis/8/88 PB2 gene (see Gorman, *J Virol* 64:4893–4902(1990)), which also contained BamHI and BsmI restriction sites. The sequence of PB2003 is shown in Table 1 below.

First strand cDNA was synthesized using Superscript II reverse transcriptase (Gibco/BRL, Bethesda, Md.) in the reaction buffer provided by the manufacturer, 0.5 mM each deoxy-nucleotide triphosphate (dNTPs; Promega, Madison, Wis.), and 2 units/$\mu$l RNAsin (Promega), at 42° C. for 2 hours. The cDNA was purified by phenol/chloroform extraction, and chromatographed over an S-300 HR microcolumn (Pharmacia, Piscataway, N.J.). The cDNA was then amplified, using the polymerase chain reaction (PCR), in two segments, both of which comprised the unique NcoI site at position 1229. The C-terminal clone was prepared using oligonucleotide primers PB2003 and PB2005 (vRNA sense, positions 1257–1276; see table 1 for the sequence of PB2005). The N-terminal clone was made using primers PB2002 (vRNA sense, containing an XbaI restriction site, the T3 promoter sequence, and 28 nts from the 5' end of PB2 vRNA) and PB2004 (mRNA sense, positions 1126–1146). The sequences of PB2002 and PB2005 are shown in Table 1.

PCR was carried out in a Perkin Elmer (Norwalk, Conn.) thermal cycler, in 1X PCR buffer II (Perkin Elmer) containing 2 mM MgCl$_2$, 0.2 mM dNTPs, 0.2 µM each primer, and 2.5 units Taq polymerase, by performing 50 cycles of denaturation at 94° C. for 1 minute, annealing at 40° C. for 2 minutes, and extension at 72° C. for 3 minutes, followed by incubation at 72° C. for 30 minutes. The PCR-generated fragments were phenol/chloroform extracted, ethanol precipitated, and electrophoresed in a 1% low-melting point agarose gel (FMC, Rockland, Me.) for 100 volt-hours in 1 X TAE buffer (40 mM Tris-acetate, 1 mM EDTA, pH 8.0). The DNA fragments of the expected sizes (1.29 kb for the N-terminal fragment, and 1.24 kb for the C-terminal fragment) were excised from the gel, the gel slice was melted, and the DNA extracted using the "QN+" procedure as described (Langridge, Anal Biochem 103:264–71 (1980)). An aliquot of each purified DNA was used for ligation to the pCRII TA-cloning vector (InVitrogen, San Diego, Calif.) using T4 DNA ligase (New England Biolabs, Beverly, Mass.). An aliquot of the ligation mixture was used to transform competent *E. Coli* DH5 cells (Gibco/BRL, Bethesda, Md.). Individual colonies were screened for the presence of the inserts by standard techniques.

Sequencing of the PB2 gene inserts was performed, using primers whose sequence was based on that of the A/Memphis/8/88 PB2 gene, by dideoxy chain termination sequencing of double-stranded plasmid DNA with Sequenase (USB, Cleveland, Ohio.). The sequence of two independent clones for each fragment was determined and found to be identical except for a one nucleotide deletion in one of the N-terminal clones, which was discarded since it is predicted to cause a frameshift mutation in the open reading frame encoding PB2. As expected, the sequence was highly homologous to that of the A/Memphis/8/88 PB2 gene, with only 1 1 nucleotide and 3 amino acid differences. The A/Memphis/8/88 PB2 sequence is disclosed in Gorman, *J Virol* 64: 4893–4902 (1990). Sequence differences between A/Memphis/8/88 (as reported in GenBank) and A/LA/2/87 PB2 genes were found at nucleotide positions (counting from the first nucleotide of the cRNA(+) sense strand): 80 (G in Memphis/8/88 and A in A/LA/2/87), 81 (A in Memphis/8/88 and G in A/LA/2/87), 306 (T in Memphis/8/88 and C in A/LA/2/87), 338 (A in Memphis/8/88 and C in A/LA/2/87), 504 (C in Memphis/8/88 and A in A/LA//87), 505 (A in Memphis/8/88 and C in A/LA/2/87), 543 (T in Memphis/8/88 and G in A/LA/2/87), 886 (C in Memphis/8/88 and A in A/LA/2/87), 887 (A in Memphis/8/88 and C in A/LA/2/87), 990 (G in Memphis/8/88 and A in A/LA/2/87), 1164 (A in Memphis/8/88 and G in A/LA/2/87), 1179 (T in Memphis/8/88 and C in A/LA/2/87) and 1929 (T in Memphis/8/88 and C in A/LA/2/87). Resequencing of a small portion of the Memphis/8/88 cDNA uncovered two errors, at positions 80 and 81, in the GenBank sequence; the sequence at these positions is the same as that of A/LA/2/87. Three of the nucleotide differences resulted in amino acid differences in A/LA/2/87, at amino acid positions 104, 160, and 287.

The full-length PB2 cDNA was then re-constructed by digestion of the C-terminal clone with BamHI and NcoI, and of the N-terminal clone with XbaI and NcoI. The DNA fragments released by the digestion were gel purified using the QN+ procedure and ligated into a BamHI/XbaI-digested pUC19 standard cloning vector.

TABLE 1

Oligonucleotide sequences used in Examples 1, 2 and 5.

Sequences are listed 5' to 3'

| | |
|---|---|
| PB2002 | GCGCGCTCTAGAATTAACCCTCACTAAAAGTAGAAACAAGGTCGTTTTTAAACTAT |
| PB2003 | GCGCGCGGATCCGAATGCGAGCAAAAGCAGGTCAATTATATTC |
| PB2004 | GGGAAAAGGGCAACAGCTATA |
| PB2005 | CACCTCTAACTGCTTTTATC |
| PB2006 | GAAAAAGCACTTTTGCATC |
| n2pb2.4 | AAGAGCCACAGTATCAGCAG |
| W537F | GGGCCGTTAATCTCGAACATCATTGACGAAGAGTAAGTTATTG |
| W552F | ATTTCTGATGATGAATTGATACGTATTGACCAACACCG |
| W557F | GAATTTTAACAGTTTCGAAGTTTCTGATGAT |
| W564F | CAACATTGCAGGGTTCTGAGAGAATTGAATTTTAACAGTTTC |
| E65G | CAAAAGGATAACAGGCATGGTACCGGAGAGAAATG |
| P112S | CCTTTCGACTTTGTCAAAATAAGTCTTGTAGACTTTGCTATAGTGCACCGTATTTGTCAC |
| N265S | CCTAATTATTGCAGCCCGGTCGATAGTGAGAAGAG |

EXAMPLE 2

Mutagenesis of the PB2 cDNA

We identified 10 native tryptophan residues in the amino acid sequence of the influenza A/LA/2/87 PB2 protein. Using the cDNA cloned in Example 1, we constructed PB2 variant cDNAs containing specific, site-directed modifications as follows.

A summary of the positions of the tryptophan and ts residues and the amino acid modifications introduced into the cloned PB2 cDNAs from Example 1 is presented in Table 2. In all cases the tryptophan residue was replaced with a phenylalanine residue. The possibility of a spontaneous reversion is minimal, since the codons for phenylalanine (TTT or TTC) differ by two nucleotides from that for tryptophan (TGG). In all cases, other translationally silent mutations were made in order to introduce restriction enzyme (RE) changes for the purpose of tracing the various alleles.

PB2 cDNAs containing the tryptophan modifications and the E65G and N265S mutations were generated using the Chameleon Site Directed Mutagenesis Kit (Stratagene, La Jolla, Calif.). The temperature sensitive P112S mutation was created by cassette mutagenesis using fragments amplified by PCR. The mutagenic primer (P112S, see Table 1) which contained the sequence of a nearby unique restriction site (TthIII 1), as well as the sequence of the mutations, was used in conjunction with a primer of opposite sense distal to another unique restriction site (BamHI). The BamHI-TthIII1 fragment in the wild-type PB2 cDNA was then replaced with the analogous P112S fragment from the PCR reaction.

TABLE 2

Amino Acid changes in LA tryptophan mutants

| Name | | | | | |
|---|---|---|---|---|---|
| A. Single Mutants | | | | | |
| | Amino acid position | Wild type amino acid | Wild type codon | Mutant amino acid | Mutant Codon |
| E65G | 65 | E | GAA | G | GGC |
| P112S | 112 | P | CCA | S | AGC |
| N265S | 265 | N | AAC | S | TCG |
| W552F | 552 | W | TGG | F | TTC |
| W557F | 557 | W | TGG | F | TTC |
| W564F | 564 | W | TGG | F | TTC |
| B. Combination Mutants | | | | | |
| | Mutations | | | | |
| 3ts | E65G, P112S, N265S | | | | |
| 3WF | W552F, W557F, W564F | | | | |
| 3ts/3WF | E65G, P112S, N265S, W552F, W557F, W564F | | | | |

EXAMPLE 3

Preparation of Viral RNP

Viral ribonucleoprotein (RNP) was purified from A/PR/8/34 virus grown in SPF eggs using the protocol described in Parvin, *J Virol* 63:5142–5152(1989), with certain modifications, as disclosed below.

Six to seven hundred SPF eggs were injected with approximately $10^4$ pfu of the influenza A/PR/8/34 virus and incubated at 35° C. for 2 days. After chilling to 4° C. overnight, allantoic fluid was harvested and concentrated approximately 10-fold using an Amicon Hollow Fiber Cartridge (Type H1P100-20) and an Amicon LP-1 pump. Virus was pelleted by centrifugation in a SW28 rotor at 25,000 rpm for 90 minutes at 4° C., resuspended in 100 mM NaCl, 10 mM Tris-HCl, pH 7.5, 10 mM EDTA (NTE buffer), and re-pelleted twice through a 30% sucrose cushion (25,000 rpm in a SW28 rotor for 2.5 hours, then 36,000 rpm in a SW50.1 rotor for 90 minutes).

The viral pellet was resuspended in 0.1 M Tris, pH 8.1, 0.1 M KCl, 5 mM $MgCl_2$, 5% glycerol, 1.5% Triton-N 101, 10 mg/ml lysolecithin (freshly added), and 1.5 mM dithiothreitol (DTT), to a final protein concentration of 3 mg/ml, and incubated at 37° C. for 30 minutes. Disrupted virus was concentrated on an Amicon Centriprep-10 concentrator for 1–3 hours at 3000 rpm in a Beckman J-6B centrifuge. Viral cores were purified on a three-layer glycerol step gradient (33%, 50%, and 70% glycerol) centrifuged in a SW50.1 rotor at 45,000 rpm, 4° C., for 4 hours. Fractions of 0.3 ml were harvested from the gradient and analyzed by SDS-polyacrylamide gel electrophoresis (SDS-PAGE).

Fractions enriched in NP protein were pooled and centrifuged through a CsCl/glycerol step gradient (three layers: 1.5 M CsCl/30% glycerol, 2.0 M CsCl/35% glycerol, and 2,5 M CsCl, 40% glycerol), in a SW50.1 rotor at 45,000 rpm for 24 hours at 4° C. Again, fractions enriched in NP protein were pooled, and dialyzed to a final buffer composition of 50% glycerol, 50 mM Tris pH 7.5, 100 mM NaCl, 10 mM $MgCl_2$, and 1 mM DTT using dialysis tubing with a molecular weight cut-off of 50,000 daltons. The protein concentration of various RNP preparations ranged from 1 to 2 mg/ml. RNPs were stored at −80° C. The activity of the RNP was determined by NA rescue using the WSN-HK helper virus according to the method of Enami, *Proc Natl Acad Sci* 87:3802–05(1990) and the protocol outlined below, except that 0.1 $\mu g/\mu l$ RNP was used and the virus obtained was plaqued on MDBK cells in the absence of trypsin. The transfection yield was usually $5–10\times10^4$ pfu.

EXAMPLE 4

Transfection of the PB2 Variant cDNAs and Rescue of Recombinant PB2 Virus

Wild-type influenza A/LA PB2 cDNA and the eight influenza A/LA PB2 cDNA variants constructed in Example 2 were rescued into influenza virus using a modified version of the reverse genetics protocol originally described by Palese and co-workers (see, for example, Enami and Palese, *J Virol* 65:2711–13(1991)) and employing a host-range mutant PB2 helper virus, as described by Murphy and colleagues in Clements, *J Clin Microbiol* 30:655–62(1992) and Subbarao, *J Virol* 67:7223–28(1993). The PB2 host-range helper virus is a single gene reassortant virus containing the PB2 gene from A/Mallard/NY/6750/78 and the remaining seven genes from A/LA/2/87. It was obtained from Dr. L. Potash (DynCorp/PRI, Rockville Md.) and grown in SPF eggs.

This PB2 helper virus had been used previously for rescue by transfection of primary chick kidney (PCK) cells (see Subbarao, *J Virol* 67:7223–28(1993)), since the virus is a host-range mutant which can grow productively in PCK cells but does not form plaques in mammalian cells. See Clements, *J Clin Microbiol* 30:655–62 (1992). Surprisingly, we found that the mammalian cell line, MDBK, could be infected with the virus and could support the expression of a transfected reporter gene (chloramphenicol acetyl transferase, CAT) which is dependent on influenza polymerase function for expression (IVACAT). See Luytjes, *Cell* 59:1107–13(1989).

In addition, we employed an improved transfection method which uses electroporation of MDBK cells and yields equal or greater numbers of transfectant viruses with a 10-fold reduction in replication of helper virus compared to the previously described DEAE-dextran transfection procedure (See Li, Virus Res 37:153–61(1995) and U.S. Ser. No. 08/316,049 filed Sep. 30, 1994, herein incorporated by reference). The electroporation technique also appeared to eliminate another source of background, namely, the rescue of the RNA encoding PB2 from A/PR/8/34, which is present in low amounts in the RNP preparation. Instead of PCK cells we therefore used electroporation of MDBK cells for PB2 rescue experiments.

MDBK cells were obtained from the ATCC, Rockville, Md. Sub-confluent monolayers of MDBK cells (one 60 mm dish per transfection) were infected with the helper virus diluted in phosphate-buffered saline (PBS; JRH BioSciences, Lenexa, Kans.) to give a multiplicity of infection (moi) of 5, for 1 hour at room temperature. The infected cells were removed from the dish by applying 0.4 ml of pre-warmed (37° C.) 0.5% trypsin (JRH) for 2 minutes at room temperature. The trypsin was inactivated by adding 2 mg soybean trypsin inhibitor (Sigma) in PBS containing $Mg^{+2}$ and $Ca^{+2}$ (JRH). The infected cells were pelleted at 2000 rpm in a Beckman tabletop clinical centrifuge for 5 minutes at room temperature, and resuspended in 0.3 ml PBS. The cells were transferred to an electroporation cuvette (0.4 cm gap, Bio-Rad, Hercules, Calif.). vRNA-sense RNP was prepared by in vitro transcription of the BsmI-linearized PB2 cDNA (2 μg per transcription) with T3 polymerase (2 units/μl, Stratagene, LA Jolla, Calif.) in the presence of 0.5 mM each nucleotide triphosphate (Promega, Madison, Wis.), 1 unit/μl RNAsin (Promega), and 0.2–0.4 /μg/μl purified RNP protein. Transcriptions were incubated at 37° C. for 45 minutes, followed by treatment with RQ1 DNase (Promega) at 37° C. for 5 minutes. The RNP mixture was added to the infected cells in the cuvette and immediately electroporated with one pulse at 250 mV, 500 /μF using a Bio-Rad (Hercules, Calif.) Gene Pulser. The electroporated cells were then re-plated in 2 ml of MEM (JRH) containing 1% bovine serum albumin (BSA; Gibco/BRL, Grand island, N.Y.) and 1.25 μg/ml L-(tosylamido-2-phenyl)ethyl chloromethyl ketone (TPCK)-treated trypsin (Worthington Biochemical Corp., Freehold, N.J.) and incubated overnight at 34° C.

The supernatant was harvested and used undiluted to infect confluent monolayers of MDCK cells in 10-cm dishes (two per transfection), which were then overlaid with 0.8% agarose in L-15 medium (JRH) containing 2.5 μg/ml TPCK-trypsin and incubated at 34° C. for three days. Plaques were picked into 0.5 ml of MEM/1% BSA, dispersed with a pipette, and 0.1 ml of the plaque dispersion was used to infect MDCK cells in 24-well dishes. The infected MDCK cells were incubated at 34° C. for 2–3 days and screened for recombinant virus as described in Example 5 below.

EXAMPLE 5

RT/PCR Screening for Recombinant Virus

Supernatants from wells showing cytopathic effects (CPE), i.e., cell elongation and rounding, followed by cell detachment and death, were harvested and treated with RQ1 DNase at 37° C. for 10 minutes to prevent carryover of trace amounts of input cDNA. vRNA was prepared by PK treatment of the medium followed by phenol/chloroform extraction and ethanol precipitation as described in Example 1 above. One third of the RNA was used for RT/PCR screening, employing the primers n2pb2.4 and PB2006 (see Table 1 for the sequences of these primers). These primers are able to amplify a short region of the PB2 gene from the three strains used in these experiments (A/LA/2/87, A/PR/8/34, or A/Mallard/NY/6750/78). First strand cDNA was synthesized using Superscript II reverse transcriptase (Gibco/BRL, Bethesda, Md.) in the reaction buffer provided by the manufacturer, 0.1 mM each deoxy▲nucleotide triphosphate (dNTPs; Promega, Madison, Wis.), 1 μM n2pb2.4 primer, and 2 units/ml RNAsin (Promega), at 42° C. for 30 minutes. The reaction mixture was adjusted to 1 X PCR buffer II (Perkin Elmer), 2 mM $MgCl_2$, 0.2 mM dNTPs, 0.2 μM each primer, and 2.5 units Taq polymerase. PCR was carried out in a Perkin Elmer (Norwalk, Conn.) thermal cycler. Thirty-five cycles of denaturation at 94° C. for 1 minute, annealing at 50° C. for 1 minute, and extension at 72° C. for 2 minutes, were performed, followed by incubation at 72° C. for 30 minutes.

The PCR fragments generated using these primers were characterized by digestion with HinfI (New England Biolabs, Beverly, Mass.), which produces different sized digestion products that are diagnostic for the PB2 genes of the three strains as shown in Table 3 below.

TABLE 3

| PB2 RT/PCR HinfI digestion fragment sizes (bp) | | |
|---|---|---|
| A/LA/2/87 | A/PR/8/34 | A/Mallard/NY/78 |
| 331 | 176 | 360 |
| 149 | 163 | 80 |
| 56 | 129 | 68 |
|  | 56 | 28 |
|  | 12 |  |

PB2 variant viruses from plaques that were identified as having the variant A/LA/287 PB2 RNA sequences were plaque-purified in MDCK cells, passaged once in MDCK cells at 34° C. (in MEM+trypsin, 2–3 days), re-screened by RT/PCR and HinfI restriction analysis as above and then grown in SPF eggs (SPAFAS) at 35° C. The RT/PCR demonstrated that three of the four PB2 variant influenza viruses were successfully transfected and rescued using the foregoing techniques (W552F, W557F, and W564F). Variants containing all three of the foregoing mutations (termed "3WF"), as well as the three foregoing mutations in combination with temperature sensitive mutants E65G, P112S, and N265S (termed "3ts/3WF") were also rescued analogously.

EXAMPLE 6

Determination of Temperature Sensitivity

Stocks of the PB2 variant viruses from Example 5 above were titrated by plaque assay in MDCK cells at 34° C. (permissive temperature) in a $CO_2$ incubator, or at 37, 38, 39 or 40° C. in Nalgene bio-containers (Nalge, Rochester, N.Y.) submerged in water baths whose temperatures were tightly regulated by Lauda constant temperature immersion circulators (Fisher Scientific, Sunnyvale, Calif.). The water baths maintained the desired temperatures within a 0.1° C. range. The water-tight containers were purged with 5% $CO_2$, 21% $O_2$, 74% $N_2$ (BioBlend; Altair, San Ramon, Calif.) before closing. Shut-off temperature was defined as the lowest temperature at which a 100-fold or greater reduction in the efficiency of plaquing (EOP) is observed, relative to that observed at 34° C.

A virus was defined as being temperature sensitive if the plaque size was reproducibly reduced at elevated temperatures and/or if the EOP was reduced 10-fold or more at 39° C. EOP and plaque morphology were analyzed at temperatures ranging from 37 to 40° C. The EOP of the parental A/LA/2/87 virus or of the wild-type transfectant ("LA wt") used as controls varied less than 2-fold over this range. The results are shown in Table 4 below.

TABLE 4

Phenotypes of PB2 tryptophan mutant viruses in MDCK cells

| Virus | Titer in eggs ($\log_{10}$ pfu/ml) | Plaque size at 39° C. | Plaque size at 40° C. | Shut-off temperature |
|---|---|---|---|---|
| A/LA/2/87 | 8.4 | large | large | >40° C. |
| LA wt | 8.4 | large | large | >40° C. |
| W552F | 8.6 | large | small | >40° C. |
| W557F | 7.5 | small | tiny | >40° C. |
| W564F | 8.0 | small | tiny | >40° C. |
| 3WF | 8.0 | small | tiny | 40° C. |
| 3ts | 8.0 | small | tiny | 40° C. |
| 3ts/3WF | 8.0 | tiny | none | 38° C. |

[1]plaque diameter (after 3 days incubation): large = 2–3 mm; small = 1–2 mm; tiny = ≦1 mm The above data demonstrates that the mutation of any one of these three tryptophan residues leads to a mild ts phenotype (plaque size reduction at 39–40° C.), and that the combination of all three mutations ("3WF") causes a marked ts phenotype, with the virus showing a 100-fold reduction in EOP at 40° C. A virus containing a PB2 gene with the 3 ts mutations, E65G, P112S and N265S ("3ts") has a ts phenotype similar to that of 3WF. Further, when 3ts and 3WF were combined ("3ts/3WF"), the virus exhibits a shut-off temperature of 38° C., and is unable to form plaques at 40° C.

EXAMPLE 7

Determination of Attenuation in Mice

Three to four week old Balb/c mice were anesthetized with Metafane and infected intranasally with $2\times10^5$ pfu each virus in a volume of 50 ml, diluted in PBS containing 1% bovine serum albumin (BSA), in groups of five to ten. While not all mutants were tested at the same time, a control group infected with the wild-type PB2 transfectant virus was included in each experiment, and the results obtained did not vary significantly between experiments. Three days after infection, mice were euthanized with $CO_2$ gas and their lungs and nasal turbinates were removed. Homogenates were prepared in EMEM supplemented with 2 mM glutamine, 200 units/ml penicillin, 0.2 mg/ml streptomycin, and 200 units/ml nystatin. To approximate a 10% suspension nasal turbinates were homogenized in 1 ml, and lungs in 2 ml. After clarification by low-speed centrifugation, the virus present in the samples was quantitated by $TCID_{50}$ assay on 96-well dishes of MDCK cells in the presence of 2.5 mg/ml TPCK-trypsin at 34° C. Titers were calculated by the method of Karber and expressed as the $log_{10}$ of the $TCID_{50}$ per gram of tissue. The limit of detection of this assay is 2.2 $log_{10}$ $TCID_{50}$ per gram. Since each positive well increases the titer by 0.25 logs, samples not showing any CPE were assigned a value of 1.95. The means of the $log_{10}$ $TCID_{50}$ per gram values, the standard errors of the mean (SEM) for each group, and P values (unpaired t-test) were determined using StatView software (Abacus Concepts Inc., Berkeley, Calif.).

TABLE 4

Replication of PB2 Mutant Viruses in Balb/c Mice

| Virus | Shut-off Temp. | Turbinate titer ± SE $Log_{10}$ $TCID_{50}$/g | lung titer ± SE $Log_{10}$ $TCID_{50}$/g |
|---|---|---|---|
| LA wt | >40° C. | 5.37 ± 0.11 | 5.07 ± 0.25 |
| 3WF | 40° C. | 5.55 ± 0.09 | 2.15 ± 0.09 |
| 3ts | 40° C. | 4.85 ± 0.11 | ≦1.95 |
| 3ts/3WF | 38° C. | 3.03 ± 0.19 | ≦1.95 |

The 3WF mutant showed wild-type levels of replication in the nasal turbinates, but only barely detectable replication in lungs; only 40% of the mice had positive lung samples. The replication of the 3ts virus was slightly reduced in turbinates, and undetectable in lungs. The combination mutant, 3ts/3WF, was similarly restricted in lungs, but also grew to levels which were over 100-fold lower compared to the wild-type. Thus, the various transfectant viruses show varying levels of growth attenuation in mice.

EXAMPLE 8

Determination of Attenuation in Ferrets

Six to twelve week old, male, castrated ferrets, prescreened for antibodies to influenza and treated with penicillin for 7 days (30,000 units per day) were obtained from Triple F Farms (Sayre, N.J.). Ferrets were anesthetized with diethyl ether and infected intranasally with approximately $3\times10^7$ egg infectious dose 50% ("$EID_{50}$ ") virus in an inoculum of 1 ml (0.5 ml in each nostril). The body temperature of the infected ferrets was determined rectally twice daily for three days. The normal body temperature of uninfected ferrets is 102.2 F. Fever is defined as a temperature of 103.8 F or above. After 3 days the ferrets were euthanized via heart puncture with sodium pentobarbital (130 mg/ferret) and the lungs and nasal turbinates were removed. Tissue suspensions (10% w/vol) were prepared by homogenization in Hank's balanced saline solution containing 2 ×Basal Eagle Media (BME) Amino Acids, 2×BME Vitamins, 4 mM L-Glutamine, and 0.05 mg/ml Gentamycin sulfate. Viral titers were determined using the $EID_{50}$ assay, and $log_{10}$ $EID_{50}$, ml values calculated according to Reed and Muench. Values were expressed as the $log_{10}$ of the $EID_{50}$ per gram of tissue; the lowest measurable amount of virus was 3.0 $log_{10}$ $EID_{50}$/g. Statistical analysis was performed as described above.

TABLE 5

Ferret temperatures (°F.) after infection with PB2 Mutant Viruses

| | | Ferret Number | | | |
|---|---|---|---|---|---|
| A. Infection with PB2 Mutant Virus 3ts/3WF | | | | | |
| | | 414 | 416 | 420 | 421 |
| day 1 | AM | 102.8 | 103.0 | 102.6 | 102.8 |
| | PM | 102.4 | 102.2 | 102.0 | 102.2 |
| day 2 | AM | 102.8 | 104.2 | 103.2 | 103.0 |
| | PM | 101.6 | 103.2 | 101.6 | 101.0 |

TABLE 5-continued

Ferret temperatures (°F.) after infection with PB2 Mutant Viruses

Ferret Number

|       |    |       |       |       |       |
|-------|----|-------|-------|-------|-------|
| day 3 | AM | 102.2 | 103.0 | 102.6 | 102.6 |

B. Infection with control LA Wild Type Virus

|       |    | 419   | 425   | 552   | 555   |
|-------|----|-------|-------|-------|-------|
| day 1 | AM | 104.2 | 105.0 | 104.4 | 104.2 |
|       | PM | 102.4 | 103.6 | 103.2 | 102.2 |
| day 2 | AM | 103.4 | 103.6 | 103.0 | 103.4 |
|       | PM | 102.6 | 103.0 | 101.6 | 102.4 |
| day 3 | AM | 102.4 | 102.2 | 102.6 | 103.2 |

TABLE 6

Replication of PB2 Mutant Viruses in Ferrets

| Virus   | # with fever/ # infected | Nasal turbinate titer ± SE $\log_{10}EID_{50}/g$ | Lung titer ± SE $\log_{10}EID_{50}/g$ |
|---------|--------------------------|--------------------------------------------------|----------------------------------------|
| LA wt   | 4/4                      | 7.16 ± 0.17                                      | <3.0                                   |
| 3ts/3WF | 1/4                      | 5.54 ± 0.11                                      | <3.0                                   |

In contrast to the ferrets infected with the wild-type virus, which all showed a febrile response on the morning of the first day after infection (see Table 5B.), the 3ts/3WF transfectant virus induced fever in only one (3416) out of four ferrets, which was on the morning of the second day after infection (Table 5A.). In addition, the 3ts/3WF mutant replicated to 40-fold lower titers in the nasal turbinates (see Table 6). The wild-type virus was not detected in the lungs of any of the ferrets, thus precluding any conclusions about the significance of the absence of lung virus in ferrets infected with the mutant. However, the temperature data and nasal turbinate replication data support the conclusion that the level of attenuation shown by the 3ts/3WF virus approaches that which is desired in a live virus vaccine.

EXAMPLE 9

Phenotypic Stability in Nude Mice

To determine whether the attenuated phenotype of 3ts/3WF was stable after an extended period of replication in an animal model, nude mice were used, since replication can continue for up to 14 days in these animals. As a control, a previously described ts virus, ts 1 A2 (see Background section above), was used. This vaccine candidate was developed by Murphy et al. (NIAID) in the early 1980s. It has a 37° C. shut-off temperature, and contains two point mutations (one each in PB1 and PB2). It was found to be genetically unstable in a seronegative young vaccinee (a combination of extragenic suppression, intragenic suppression, and reversion was proposed to be responsible for the loss of the ts phenotype).

Forty Balb/c nu/nu mice (3–4 weeks old) were infected intranasally under anesthesia with 105 pfu ts1A2 virus (maximum possible titer in 50 ml) or with 106 pfu 3ts/3WF on day 0. The mice were sacrificed 13 or 14 days later. Homogenates prepared from nasal turbinates and lungs were titrated by $TCID_{50}$ assay on MDCK cells at 34° C. in 96-well plates. None of the lung samples contained detectable virus ($\geq 2.2$ 1$\log_{10}$ $TCID_{50}/g$). Virus was recovered from 30 of 40 of the nasal turbinate samples from ts1A2-infected mice, and from 23 of 36 of the 3ts/3WF-infected, mice (four mice died on day 3–4 due to unknown causes). Once CPE was complete in the wells of the 96-well plate, the medium was harvested and pooled (when more than one well was positive). To determine if the viruses were still ts, they were titrated by $TCID_{50}$ assay at 34° C. and 37° C. (ts1A2), or 34° C. and 39° C. (3ts/3WF). The choice of non-permissive temperature was based on the shut-off temperature of the infecting virus. The data are summarized in Table 7.

TABLE 7

Genetic Stability in Nude Mice

| Virus   | No. mice infected | No. isolates obtained from nasal turbinates | No. isolates with partial loss of ts phenotype |
|---------|-------------------|---------------------------------------------|------------------------------------------------|
| ts1A2   | 40                | 30                                          | 3*                                             |
| 3ts/3WF | 40                | 23                                          | 0†                                             |

*reduction in $\log_{10}$ $TCID_{50}$ at 37° C. vs 34° C. < 3
†reduction in $\log_{10}$ $TCID_{50}$ at 39° C. vs 34° C. < 3

These data support the concept that a ts, attenuated virus, containing a PB2 gene with mutations in tryptophan residues that may be involved in cap-binding function, is genetically stable in the nude mouse model.

What is claimed is:

1. A recombinant influenza virus in which the amino acid sequence comprising the PB2 protein has been modified by substitution of at least one non-native amino acid for a native tryptophan residue that affects cap binding activity of PB2 in the region spanning amino acid residues 537 through 575.

2. The recombinant influenza virus according to claim 1 wherein said recombinant influenza virus is influenza A and said tryptophan residue is located at amino acid position 552, 557 or 564.

3. A recombinant influenza A virus in which the amino acid sequence comprising the PB2 protein has been modified by substitution of non-native amino acids for the native amino acids at positions 552, 557 and 564.

4. The recombinant influenza virus according to claim 2 in which the amino acid sequence comprising the PB2 protein has additionally been modified by substitution of a non-native amino acid for a native amino acid at position 65, 112 or 265.

5. The recombinant influenza virus according to claim 3 in which the amino acid sequence comprising the PB2 protein has additionally been modified by substitution of a non-native amino acid for a native amino acid at position 65, 112 or 265.

6. A recombinant influenza A virus in which the amino acid sequence comprising the PB2 protein has been modified by substitution of non-native amino acids for the native amino acids at positions 65, 112, 265, 552, 557 and 564.

7. The virus according to claim 3 wherein said virus is a reassortant virus.

8. The virus according to claim 5 wherein said virus is a reassortant virus.

9. The virus according to claim 6 wherein said virus is a reassortant virus.

10. An influenza A PB2 protein in which at least one native tryptophan residue at position 552, 557 or 564 is replaced with a non-native amino acid residue.

11. An influenza A PB2 protein in which the native tryptophan residues at positions 552, 557 and 564 are replaced with non-native amino acid residues.

12. An influenza A PB2 protein in which the native amino acid residues at positions 65, 112, 265, 552, 557 and 564 are replaced with non-native amino acid residues.

13. An RNA sequence encoding the PB2 protein of claim 10.

14. A cDNA sequence corresponding to the RNA sequence of claim 13.

15. An RNA sequence encoding the PB2 protein of claim 11.

16. A cDNA sequence corresponding to the RNA sequence of claim 15.

17. An RNA sequence encoding the PB2 protein of claim 12.

18. A cDNA sequence corresponding to the RNA sequence of claim 17.

19. An immunogenic composition comprising an immunogenically-inducing effective amount of the virus of claim 7 in admixture with a pharmaceutically acceptable carrier.

20. An immunogenic composition comprising an immunogenically-inducing effective amount of the virus of claim 8 in admixture with a pharmaceutically acceptable carrier.

21. An immunogenic composition comprising an immunogenically-inducing effective amount of the virus of claim 9 in admixture with a pharmaceutically acceptable carrier.

* * * * *

SEQUENCE LISTING

<160> NUMBER OF SEQ ID NOS: 13

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: REPLACEMENT
      CDNA SEQUENCE

<400> SEQUENCE: 1
gcgcgctcta gaattaaacc ctcactaaaa gtagaaacaa ggtcgttttt aaactat        57

-continued

```
<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 2
gcgcgcggat ccgaatgcga gcaaaagcag gtcaattata ttc            43

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 3
gggaaaaggg caacagctat a                                    21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:REPLACEMENT
      CNDA SEQUENCE

<400> SEQUENCE: 4
cacctctaac tgcttttatc                                      20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 5 gaaaagcac ttttgcatc                                        19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 6
aagagccaca gtatcagcag                                      20

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 7
gggccgttaa tctcgaacat cattgacgaa gagtaagtta ttg            43
```

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 8
atttctgatg atgaattgat acgtattgac caacaccg                              38

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 9
gaattttaac agtttcgaag tttctgatga t                                     31

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 10
caacattgca gggttctgag agaattgaat tttaacagtt tc                         42

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 11
caaaaggata acaggcatgg taccggagag aaatg                                 35

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 12
cctttcgact ttgtcaaaat aagtcttgta gactttgcta tagtgcaccg tatttgtcac      60

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:REPLACEMENT
      CDNA SEQUENCE

<400> SEQUENCE: 13
cctaattatt gcagcccggt cgatagtgag aagag                                 35